United States Patent [19]

Roth

[11] Patent Number: 4,837,865
[45] Date of Patent: Jun. 13, 1989

[54] SUN VISOR FORMED FROM A FOOD AND BEVERAGE CARRIER

[76] Inventor: Arlen L. Roth, 8150-1 Canby Ave., Reseda, Calif. 91335

[21] Appl. No.: 209,203

[22] Filed: Jun. 20, 1988

[51] Int. Cl.⁴ ............................................. A42B 1/00
[52] U.S. Cl. ...................................... 2/196; 2/209.1; 2/177; 229/904
[58] Field of Search .................. 2/177, 191, 195, 196; 229/103, 904; 206/565

[56] References Cited

U.S. PATENT DOCUMENTS

| | | | |
|---|---|---|---|
| 2,794,585 | 6/1957 | Wagner | 229/904 X |
| 3,126,140 | 3/1964 | Lizan et al. | 229/103 X |
| 4,535,928 | 8/1985 | Capo | 229/103 |

Primary Examiner—Werner H. Schroeder
Assistant Examiner—Jeanette E. Chapman
Attorney, Agent, or Firm—John Joseph Hall

[57] ABSTRACT

A disposable food and beverage carrier of conventional size which is convertible to a sun visor by having portions of its bottom and sides perforated and adapted to be torn off so that the remaining portions define a sun visor having a head band which can be secured around a person's head and with tab and slot means to secure the sun visor in a horizontal position.

3 Claims, 5 Drawing Sheets

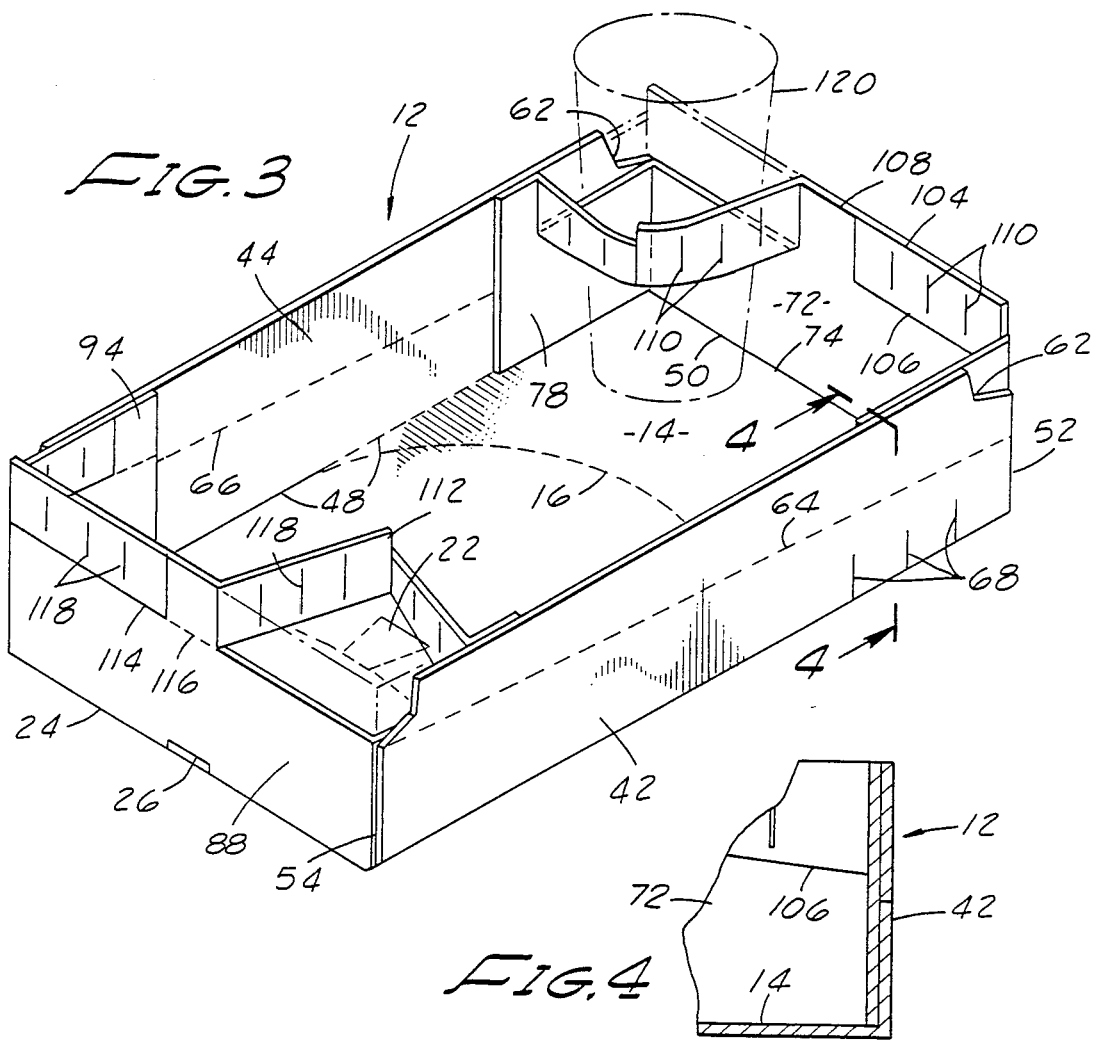
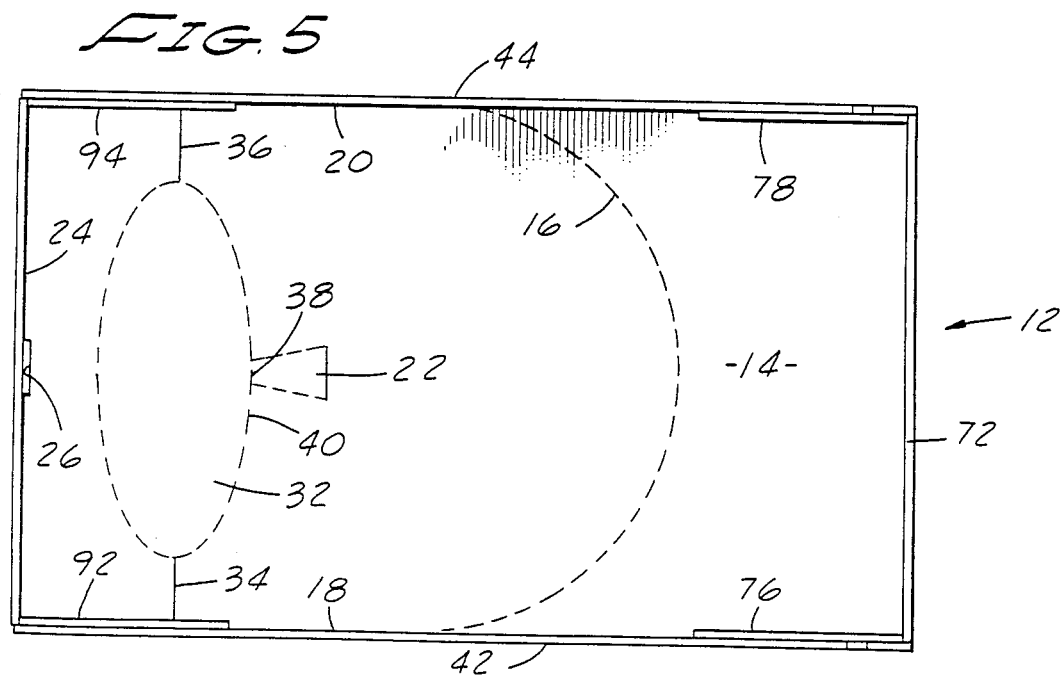

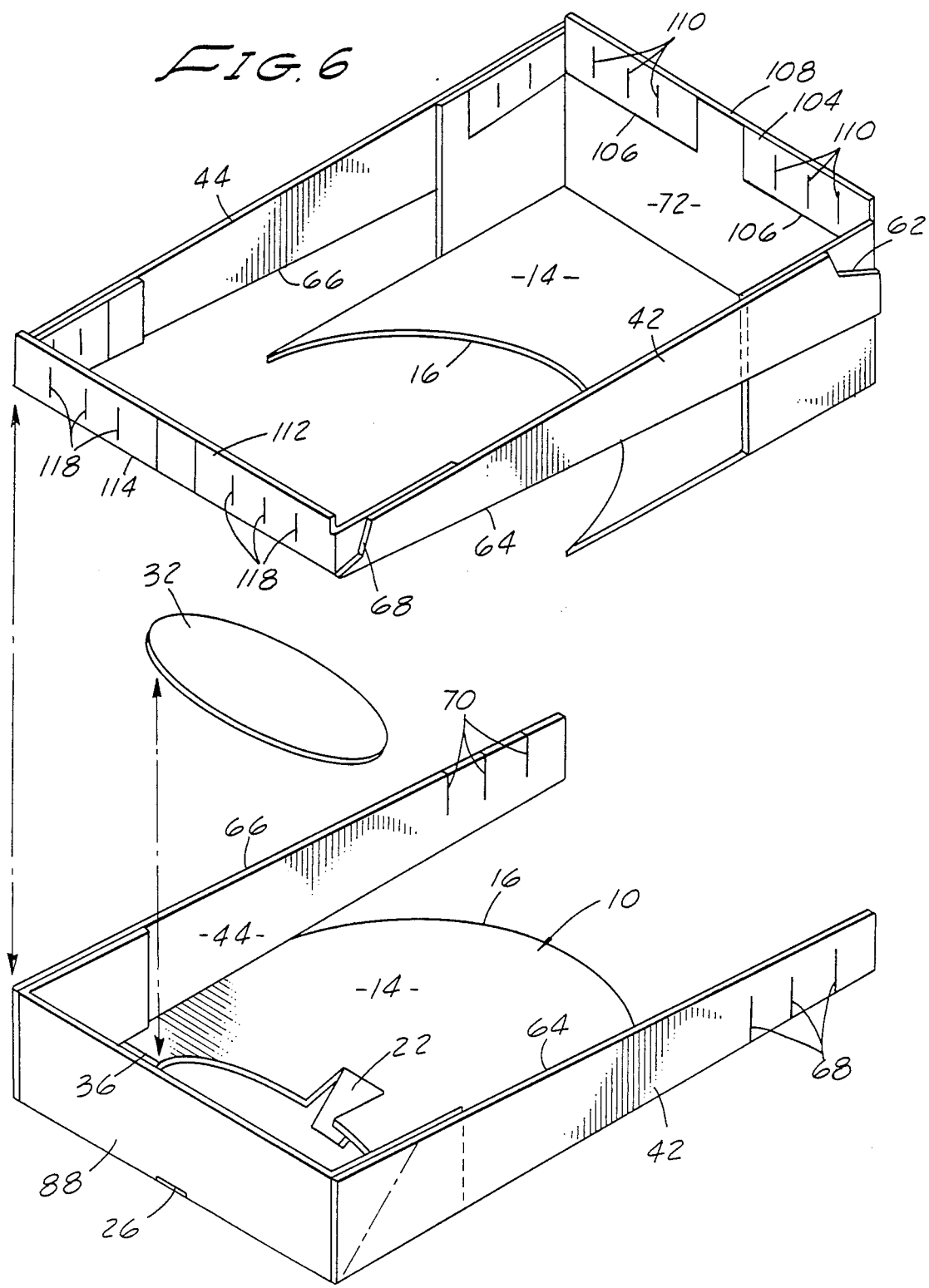

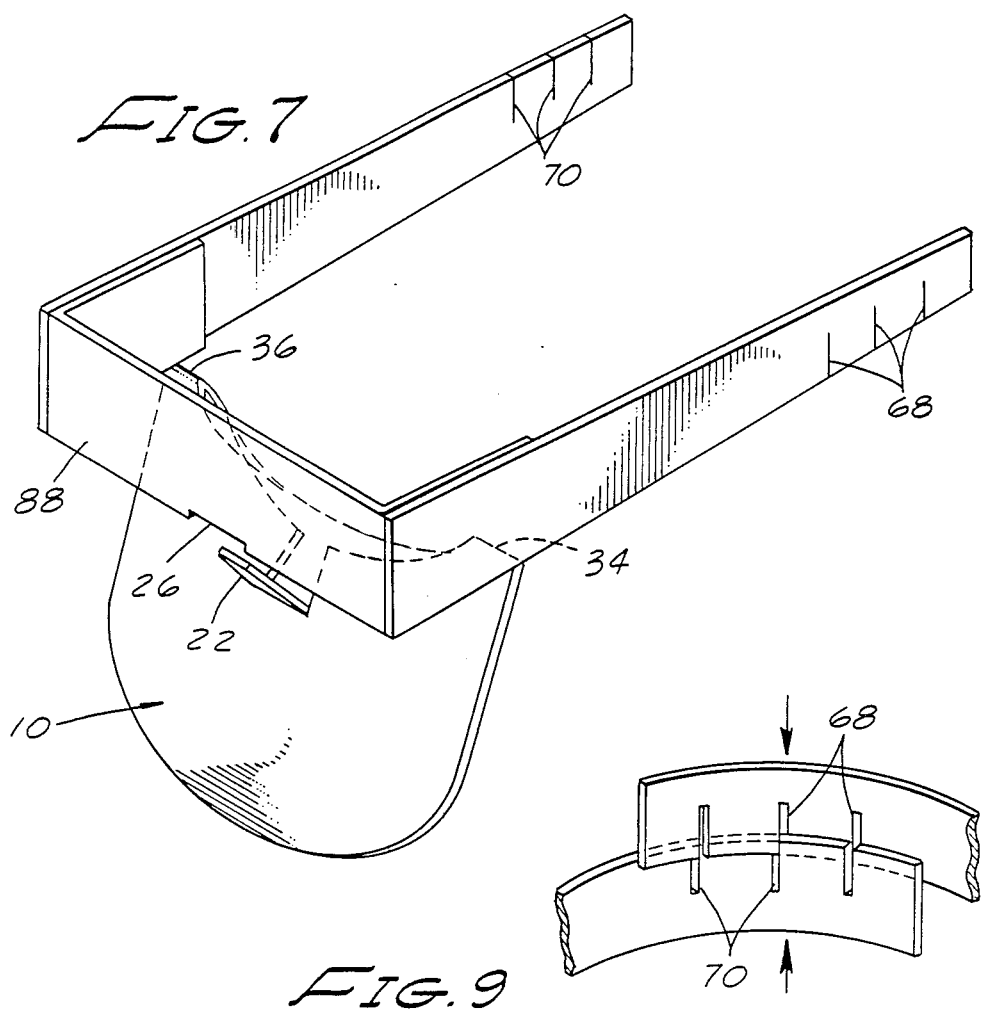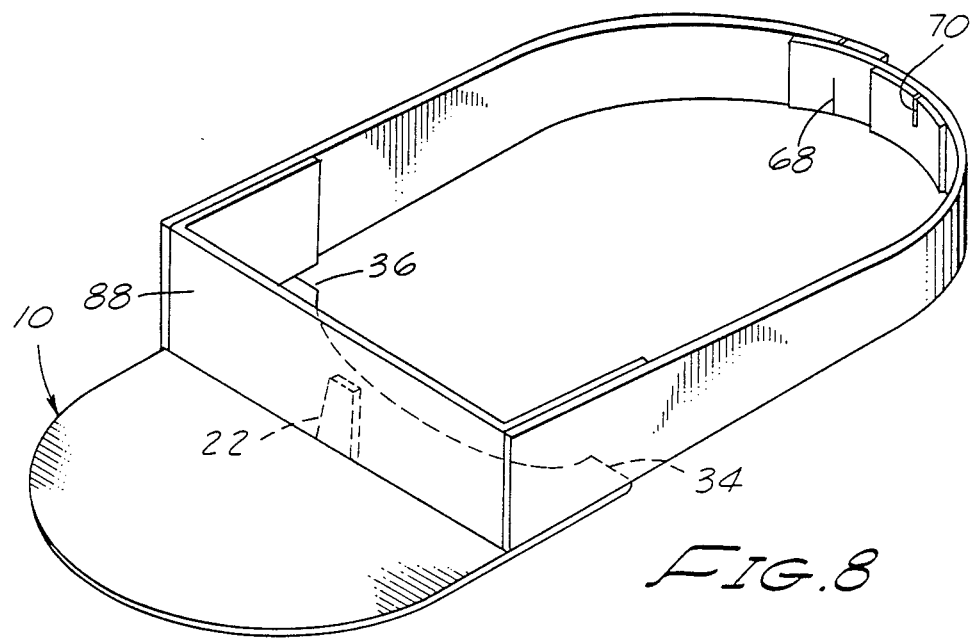

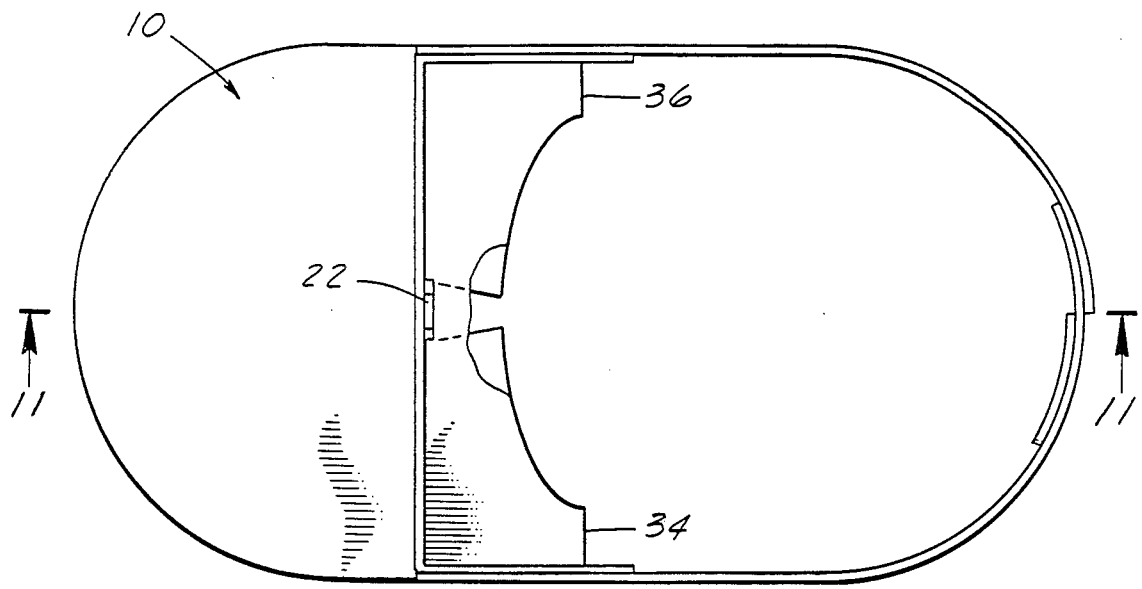
FIG. 10
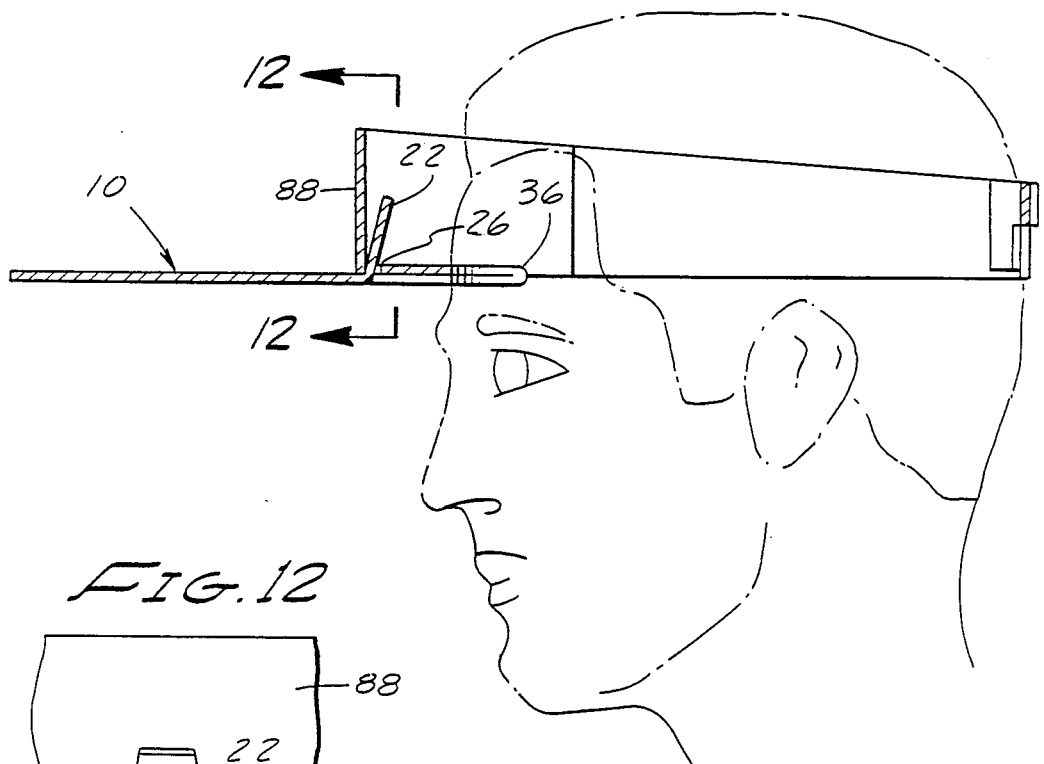
FIG. 12
FIG. 11
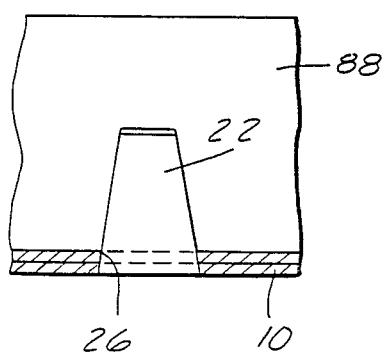

SUN VISOR FORMED FROM A FOOD AND BEVERAGE CARRIER

BACKGROUND OF THE INVENTION

1. Field of the Invention

The present invention relates to the formation of a sun visor cap construction from a conventional size disposable food and beverage carrier, made of cardboard or other suitable disposable material.

2. Description of the Prior Art

Although the prior art discloses several visor cap constructions, none appears to permit the formation of a sun visor cap from a conventional size food and beverage carrier, which is of a disposable type. Thus, the visor cap in U.S. Pat. No. 3,266,056, has no disclosure of a capability of being constructed from a food and beverage container or carrier. The same is true of U.S. Pat. No. 2,787,791. Numerous sun visors or sun shields are disclosed in U. S. Pat. Nos. 4,386,126; 2,679,947; 2,009,855; 4,247,957; 2,988,743; 3,271,778; and 4,670,910, but none of these discloses a capability of construction from a conventional size food and beverage carrier, and which is of a disposable type such as that disclosed and claimed in the present application.

SUMMARY OF THE INVENTION

The present invention relates to a novel food and beverage carrier of a conventional size and made of disposable material which provides the construction of a sun visor from its component parts.

The invention provides a bottom member having perforated areas for punching out and having side flaps and end flaps with tab members, all of which can be folded to produce a food and beverage carrier of a conventional size.

After completion of its use as a food and beverage carrier, the carrier can be converted into a sun visor cap by punching out the perforated area defining the visor portion of a sun visor cap and perforated areas leaving head bands for securing the visor portion to a person's head. The invention provides for adjustment to various sizes of a person's head. A securing tab portion provides maintenance of the visor portion in a horizontal position for use in protecting against the sun.

OBJECTS OF THE INVENTION

It is, therefore, an object of this invention to provide a food and beverage carrier having a conventional size and made of disposable material such as cardboard and the like, which can be converted after completion of its use, into a sun visor construction.

Another object of this invention is to provide a food and beverage carrier which has the capability of being convertred into a sun visor construction with relative ease and speed.

A further object of this invention is to provide a food and beverage carrier which is relatively light in weight and which can can be converted into a sun visor construction without the need for special tools or equipment or any tools or equipment other than the human hand.

A still further object of this invention is to provide a food and beverage carrier which is relatively easy to construct and yet is relatively easy to convert into a sun visor construction after completion of its use as a food and beverage carrier.

These and other objects will be more readily understood by reference to the following description and accompanying drawings, in which:

FIG. 3 is a perspective view of an embodiment of the invention in an assembled condition before conversion to a sun visor, and while in use as a food and beverage carrier.

FIG. 4 is a fragmentary cross sectional view taken on lines 4—4 of FIG. 3.

FIG. 5 is a top plan view of an embodiment of the invention in an assembled condition.

FIG. 6 is an exploded perspective view illustrating the removal of component parts form an embodiment of the invention in an assembled condition preparatory to construction of the sun visor.

FIG. 7 is a perspective view of the sun visor showing the sequence of its construction.

FIG. 8 is a perspective view of an embodiment of a fully assembled sun visor.

FIG. 9 is a fragmentary perspective view showing the locking means for the head band of the sun visor.

FIG. 10 is a top plan view of an embodiment of the fully assembled sun visor.

FIG. 11 is a cross sectional side elevational view taken on lines 11—11 of FIG. 10.

FIG. 12 is a fragmentary cross sectional view taken on lines 12—12 of FIG. 11.

Figure 1:
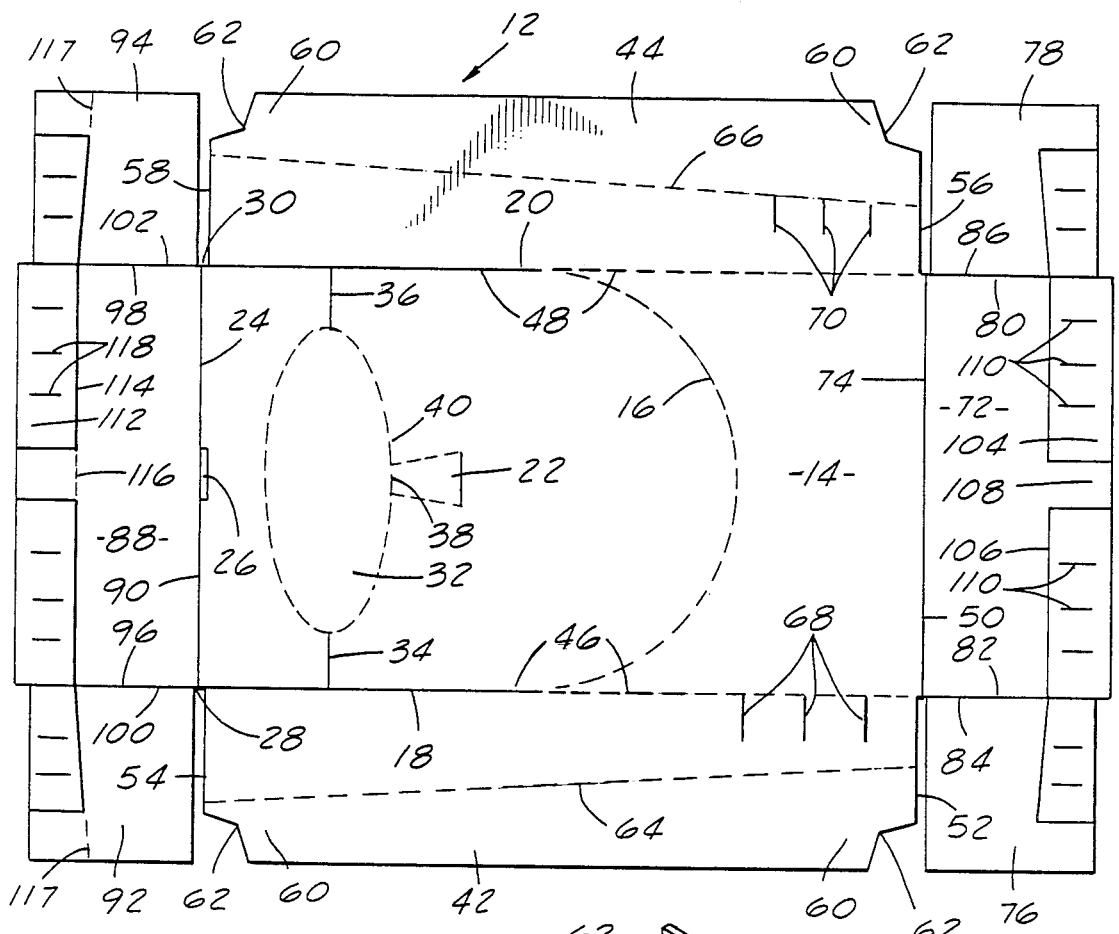
FIG. 1 is a top plan of an embodiment of the invention showing a food and beverage container in a flat, unassembled position.

The sun visor 10 is formed from a conventional sized food and beverage carrier 12, usually made of cardboard or other suitable material from a single flat piece. The invention provides a carrier 12 which is adapted in its structure for the formation of the sun visor 10 relatively easily, quickly, and without the need for tools or equipment of any kind.

In its flat or unfolded condition, the carrier 12 has a rectangular flat bottom 14 which, in a preferred embodiment, may be of a size about 7 inches wide and 12½ inches long. The middle section of bottom 14 is provided with a perforated line 16 in the form of a half circle that extends between the left side 18 and the right side 20 of bottom 14.

Bottom 14 has a tab member 22 which is initially disposed flat and is perforated on three sides and is located near the end 24 of bottom 14.

End 24 of bottom 14 is provided with a slot 26 midway between corners 28 and 30 of bottom 14. The slot is oriented in alignment with tab 22.

A perforated oval shaped member 32 adapted to be punched out is formed near end 24 and equidistant from sides 18 and 20. Oval shaped member 32 has fold lines 34 and 36 extending from each of its ends to sides 18 and 20 respectively. The top 38 of tab 22 is congruent with the middle portion of the inner side 40 of perforated oval shaped member 32.

Bottom 14 is formed with two elongated side flap members 42 and 44 generally rectangular in shape with longitudinal fold lines 46 and 48 along sides 18 and 20 of bottom 14. Fold lines 46 and 48 are perforated in the portion of their length from the intersection of half circle line 16 with sides 18 and 20 to the end 50 of bottom 14, which allows the area of bottom 14 between sides 18 and 20 and from half circle line 16 to end 50 to be punched out or otherwise separated from the rest of bottom 14.

Side flaps 42 and 44 are almost as long as bottom 14 and are preferably about 2⅞ inches wide in a preferred embodiment.

Side flap 42 has ends 52 and 54 formed at right angles to fold line 46. Side flap 44 has ends 56 and 58 formed at right angles to fold line 48. Each other corner 60 of side flaps 42 and 44 has a notch 62 cut in it.

Side flap 42 has a perforated slanted straight line 64 extending from the top portion of end 52 to the middle portion or end 54. Side flap 44 has a perforated slanted straight line 66 extending from the top portion of end 56 to the middle portion of end 58. Perforated lines 64 and 66 are adapted for tearing out the outer portions of side flaps 42 and 44.

Side flap 42 has a plurality of spaced slots 68. In a preferred embodiment, there are three slots 68 spaced equidistant from each other, parallel to each other, and at right angles to foldline 46. Slots 68 are located along the perforated portion of fold line 46 and extend from fold line 46 part way to perforated slanted straight line 64.

Side flap 44 has a plurality of spaced slots 70, preferably three in a preferred embodiment, and which are preferably spaced equidistant from each other, parallel to each other, and at right angles to fold line 48. Slots 70 are located along the portion of perforated slanted straight line 66 near side flap end 58 and extend therefrom part way toward the perforated portion of fold line 48.

Each of slots 68 is adapted to receive one of slots 70 at a time.

Bottom 14 is formed with end flap 72 at end 50 with a fold line 74. End flap 72 is formed with generally square tab members 76 and 78, preferably about 2⅞ inches square at each of its ends 80 and 82 and has fold lines 84 and 86.

Bottom 14 is formed with end flap 88 at end 24 with a fold line 90. End flap 88 is formed with generally square tab members 92 and 94, preferably about 2⅞ inches square at each of its ends 96 and 98 and has fold lines 100 and 102.

The top portion of end flap member 72 and the tab member 76 and 78 are formed to provide a strip 104 extending from the middle of end flap member 72 to a position near the outer ends of tabs 76 and 78.

The lower edge 106 of strip 104 is die cut from the lower portions of end flap member 72 and tabs 76 and 78 except for relatively short lengths 108 located at the middle of end flap 72 and the ends of tabs 76 and 78. Strip 104 is provided with a plurality of spaced vertical scorings 110 parallel to each other.

Similarly, the top portion of end flap 88 and tabs 92 and 94 are formed to provide a strip 112 extending from the middle of end flap 88 to a position near the outer ends of tabs 92 and 94.

The lower edge 114 of strip 112 is die cut from the lower portions of end flap 88 and tabs 92 and 94 except for a perforated short length 116 located at the middle of end flap 88 and perforated lengths 117 at each end of lower edge 114.

Strip 112 is provided with a plurality of spaced vertical scorings 118 parallel to each other.

Figure 2:
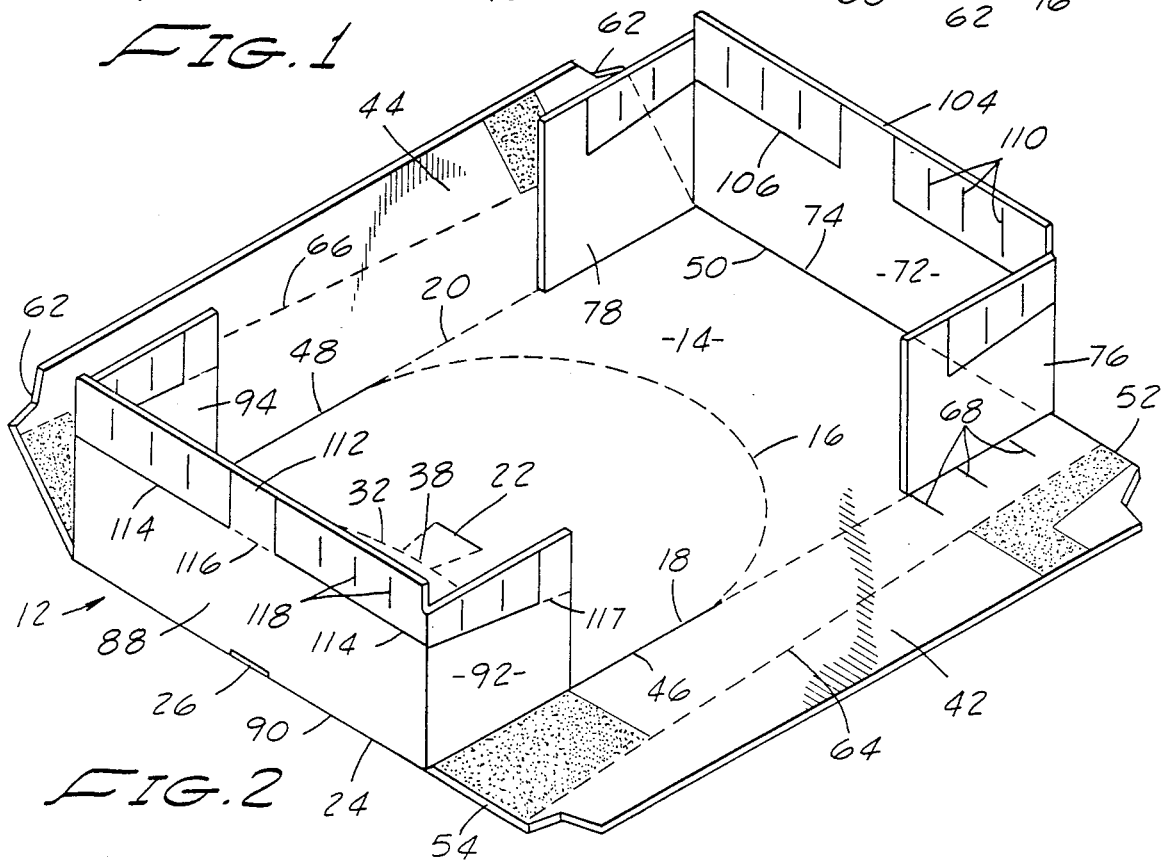
FIG. 2 is a perspective view of an embodiment of the invention showing a folding sequence of component parts of the invention.

In operation, the carrier 12 is prepared for use as a food and beverage carrier form its flat condition of one piece of material. First, end flaps 72 and 88 are folded up on fold lines 74 and 90. Tabs 76, 78, 92, and 94 are then folded as shown in FIG. 2.

Then, side flaps 42 and 44 are folded up along fold lines 46 and 48, covering tabs 76, 78, 92 and 94, which are secured by any suitable means such as gluing otherwise to side flaps 42 and 44.

The die cut portions of strips 104 and 112 are then pushed inwards to form a securing means for a beverage container or cup 120 as shown in FIG. 3. The scorings 110 and 118 provide more flexibility for strips 104 and 112.

Carrier 12 is now ready for use as a food and beverage carrier.

After completion of its use as a food and beverage carrier, carrier 12 is then ready for the construction of sun visor 10.

The sun visor 10 is produced by punching out oval shaped member 32 and tearing along perforated half circle line 16 and along perforated slanted lines 64 and 66, and removing the torn out and punched out portions.

The remaining portion of bottom 14 has the shape of a sun visor 10 and is pushed forward to assume a horizontal position as show in FIG. 8.

Tab 22 is pushed into slot 26 to maintain the sun visor 10 in a horizontal forward position. One of slots 70 of the remaining portion of side flap 44 is then inserted into one of the slots 68 of the remaining portion of side flap 42, said portions now acting as head bands for the sun visor 10, to secure the sun visor 10 around a person's head. The plurality of slots 68 and 70 provide easy adjustment of the sun visor 10 to accommodate various head sizes.

The sun visor 10 is then put into use as shown in FIG. 11.

Although I have described the invention in detail with reference to the accompanying drawings illustrating preferred embodiments of the invention, it is understood that numerous changes may be made in the details of construction and arrangement of parts without departing from the spirit and scope of the invention as hereinafter claimed.

I claim:

1. A sun visor formed from a disposable food and beverage carrier of conventional size consisting essentially of:

a food and beverage carrier having a rectangular flat bottom with two sides and a front end and a rear end and with a perforated half circle line in the middle section of said bottom and which extends to each side of said bottom to define a sun visor in conjunction with said front end of said bottom, the area thus formed extending from said half circle line to the rear end of said bottom and between said sides removable by tearing;

a perforated oval shaped member formed in said bottom and located between said front end of said bottom and said perforated half circle line and adapted to be punched out to define the rear portion of said sun visor;

a side flap member formed along each said side of said bottom and having a longitudinal fold line along its length, and having a perforated slanted straight line extending from one end of said side flap to the other end of said side flap, and having a portion of said fold line perforated between said rear end of said bottom and the intersection of said half circle line with said fold line, each side flap member forming a side of said carrier when in an assembled condition and forming a head band for said sun visor when the portion of each flap member is torn off from above said perforated slanted straight line;

an end flap member formed at said front end of said carrier and an end flap member formed at said rear end of said carrier, said front end flap member having a generally square tab member formed at each end of said front end flap member and having a fold line along said front end of said bottom, said rear end flap member having a generally square tab member formed at each end of said rear end flap member and having a fold line along said rear end, said front end flap member forming the front end of said carrer and said rear end flap member forming the rear end of said carrier, when said carrier is in an assembled condition with each tab member secured to a side flap member in said assembled condition of said carrier;

a strip member formed form the top portions of said end flap member forming the rear end of said carrier and from each tab member of said rear end flap member, said strip member having a die cut lower edge extending form near each end of each tab member to the uncut middle section of said rear end flap member;

a strip member formed from the top portions of said front end flap member forming the front end of said carrier and from each tab member of said front end flap member, said strip member having a lower edge perforated at each end of each tab member and at the middle section of said front end flap member and with its remaining length die cut from the lower portions of said front end flap member and of each said tab member; and means for securing said head band of said sun visor around a person's head formed in each said side flap member.

2. A sun visor formed from a disposable food and beverage carrier of conventional size according to claim 1 in which the means for securing said head band of said sun visor around a person's head comprises a plurality of slots in the remaining portion of each side flap member when the portion of each side flap member is torn off from above said perforated slanted straight line.

3. A sun visor formed from a disposable food and beverage carrier of conventional size according to claim 1 in which said sun visor has tab means in conjunction with a slot formed in said front end of said bottom to secure said sun visor in a horizontal position after being removed from said bottom of said carrier, said tab means having perforations around there of its sides and having its top congruent with the middle portion of the inner side of said perforated oval shaped member.

* * * * *